United States Patent
Baril et al.

(10) Patent No.: US 11,642,133 B2
(45) Date of Patent: May 9, 2023

(54) SECURING RING FOR USE WITH AN END-TO-END ANASTOMOSIS STAPLING DEVICE

(71) Applicant: Covidien LP, Mansfield, MA (US)

(72) Inventors: Jacob C. Baril, Norwalk, CT (US); Garrett P. Ebersole, Hamden, CT (US); Saumya Banerjee, Hamden, CT (US); Justin J. Thomas, New Haven, CT (US); Matthew A. Dinino, Newington, CT (US); Roy J. Pilletere, Middletown, CT (US)

(73) Assignee: Covidien LP, Mansfield, MA (US)

( * ) Notice: Subject to any disclaimer, the term of this patent is extended or adjusted under 35 U.S.C. 154(b) by 61 days.

(21) Appl. No.: 17/396,857

(22) Filed: Aug. 9, 2021

(65) Prior Publication Data
US 2023/0042225 A1    Feb. 9, 2023

(51) Int. Cl.
*A61B 17/072* (2006.01)
*A61B 17/115* (2006.01)
(Continued)

(52) U.S. Cl.
CPC .......... *A61B 17/115* (2013.01); *A61B 17/072* (2013.01); *A61B 17/1114* (2013.01);
(Continued)

(58) Field of Classification Search
CPC .............. A61B 17/068; A61B 17/0684; A61B 17/0686; A61B 17/072; A61B 17/07207;
(Continued)

(56) References Cited

U.S. PATENT DOCUMENTS

| 4,665,917 A | 5/1987 | Clanton et al. |
| 5,005,749 A | 4/1991 | Aranyi |

(Continued)

FOREIGN PATENT DOCUMENTS

| EP | 0585069 A1 | 3/1994 |
| EP | 3143949 A2 | 3/2017 |

OTHER PUBLICATIONS

International Search Report and Written Opinion dated Nov. 4, 2022, issued in corresponding international application No. PCT/IB2022/057202, 15 pages.

*Primary Examiner* — Scott A Smith
(74) *Attorney, Agent, or Firm* — Carter, DeLuca & Farrell LLP (57) ABSTRACT

A surgical kit includes a stapling device and a securing ring. The stapling device includes a reload including a trocar member and an anvil assembly including an anvil and an anvil shaft detachably couplable to the trocar member of the reload for unitary movement. The securing ring is selectively securable about the anvil shaft. The securing ring has an annular profile defining an aperture. The securing ring includes first and second portions and an intermediate portion. The first and second portions adjustably overlap each other. The first portion includes a first tab. The second portion includes a hook. The intermediate portion includes a second tab and defines slots to receive the hook of the second portion. When the first and second tabs are displaced relative to each other, the aperture is transitionable from a first state having a first diameter to a second state having a second diameter.

20 Claims, 5 Drawing Sheets

(51) Int. Cl.
*A61B 17/11* (2006.01)
*A61B 17/00* (2006.01)
*A61B 17/068* (2006.01)

(52) U.S. Cl.
CPC ......... *A61B 17/068* (2013.01); *A61B 17/0686* (2013.01); *A61B 17/07207* (2013.01); *A61B 2017/00407* (2013.01); *A61B 2017/00477* (2013.01); *A61B 2017/1103* (2013.01); *A61B 2017/1132* (2013.01)

(58) Field of Classification Search
CPC .............. A61B 17/115; A61B 17/1155; A61B 17/1114; A61B 2017/00022; A61B 2017/00477; A61B 2017/07214
USPC ..... 227/19, 175.1, 176.1, 180.1; 606/1, 139, 606/219
See application file for complete search history.

(56) References Cited

U.S. PATENT DOCUMENTS

| | | |
|---|---|---|
| 5,119,983 A | 6/1992 | Green et al. |
| 5,588,579 A | 12/1996 | Schnut et al. |
| 6,053,390 A | 4/2000 | Green et al. |
| 6,884,250 B2 | 4/2005 | Monassevitch et al. |
| 8,006,711 B2 | 8/2011 | Pietrzak et al. |
| 8,328,457 B2 | 12/2012 | Werth |
| 8,827,887 B2 | 9/2014 | Curtis et al. |
| 2009/0230170 A1* | 9/2009 | Milliman ............. A61B 17/115 227/176.1 |
| 2014/0277142 A1 | 9/2014 | Blain et al. |
| 2016/0192939 A1 | 7/2016 | Sgroi, Jr. et al. |
| 2016/0374672 A1* | 12/2016 | Bear ........................ H02J 7/00 606/219 |
| 2018/0360460 A1 | 12/2018 | Mozdzierz et al. |

* cited by examiner

SECURING RING FOR USE WITH AN END-TO-END ANASTOMOSIS STAPLING DEVICE

FIELD

The disclosure relates to a surgical device for applying surgical fasteners or staples to body tissue, and more particularly, to a securing ring for use with an end-to-end anastomosis stapling device to releasably secure an anvil to tissue.

BACKGROUND

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by end-to-end, side-to-side, or end-to-side organ reconstruction methods.

In a circular anastomosis procedure, the two ends of the organ sections are joined by means of a stapling device, which drives a circular array of staples through the end section of each organ section and simultaneously cores any tissue interior of the driven circular array of staples to free the tubular passage. Typically, these devices include an elongated shaft having a handle portion at a proximal end to actuate the device and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the device. Once the anvil shaft is secured to the device, the anvil is drawn into close approximation to the staple holding component. The device is then fired to cause the staples to pass through tissue of both sections of the organ and deform against the anvil. During the firing step, a circular knife is advanced to cut tissue inside the staple line, thereby establishing a passage between the two sections of the organ. After firing, the device is typically removed by withdrawing the anvil through the staple line.

Due to the inherent difficulty in positioning and securing the anvil assembly to tissue using, e.g., the purse-string suture, a need exists for a device that can safely and effectively secure the anvil assembly to tissue.

SUMMARY

In accordance with the disclosure, a surgical kit includes a stapling device and a securing ring. The stapling device includes a reload including a trocar member configured for axial displacement and an anvil assembly including an anvil and an anvil shaft detachably couplable to the trocar member of the reload for unitary movement. The anvil is transitionable between a spaced apart position and an approximated position configured to clamp tissue between the anvil and the reload. The securing ring is selectively securable about the anvil shaft. The securing ring has an annular profile defining an aperture. The securing ring includes first and second portions and an intermediate portion interconnecting the first and second portions. The first and second portions adjustably overlap each other. The first portion includes a first tab. The second portion includes a hook. The intermediate portion includes a second tab and defines a plurality of slots to receive the hook of the second portion. When the first and second tabs are displaced relative to each other, the aperture of the securing ring is transitionable from a first state having a first diameter to a second state having a second diameter.

In an aspect, when the first and second tabs are displaced towards each other, the first diameter may be larger than the second diameter.

In another aspect, the securing ring may be formed as a single construct.

In yet another aspect, the securing ring may be monolithically formed as a unitary construct.

In still yet another aspect, the plurality of slots of the intermediate portion may be circumferentially arranged about the securing ring.

In still yet another aspect, the hook of the securing ring may include a tapered portion configured to slide over the plurality of slots of the intermediate portion of the securing ring when the first and second tabs are displaced towards each other.

In an aspect, the hook may include a locking surface to be received in one slot of the plurality of slots of the intermediate portion of the securing ring to maintain a diameter of the aperture of the securing ring.

In another aspect, the anvil shaft of the anvil assembly may define a channel to receive the trocar member of the reload.

In yet another aspect, the intermediate portion may define an elongate slot to facilitate flexing of the securing ring.

In accordance with another aspect of the disclosure, a surgical kit includes a surgical stapling device and a securing ring. The surgical stapling device includes an adapter having an elongate shaft, a reload supported on a distal end portion of the elongate shaft, and an anvil assembly including an anvil and an anvil shaft. The reload includes a trocar member that is axially movable. The anvil shaft is releasably attachable to the trocar member. The securing ring is selectively securable about the anvil shaft. The securing ring has an annular profile defining an aperture. The securing ring includes first and second portions that at least partially overlap each other. The securing ring has tabs that are movable relative to each other, thereby selectively transitioning the aperture between a first diameter and a second diameter.

In an aspect, the securing ring may further include a ratchet mechanism to selectively maintain a diameter of the aperture.

In another aspect, the securing ring may define a circumferential slot to facilitate flexing of the securing ring.

In yet another aspect, when the tabs are displaced towards each other, a diameter of the aperture of the securing ring may be reduced.

In still yet another aspect, the securing ring may be monolithically formed.

In still yet another aspect, the anvil shaft may be movable with the trocar member as a unitary construct when the anvil shaft is coupled to the trocar member.

In still yet another aspect, the securing ring may be formed of a malleable material.

In accordance with yet another aspect of the disclosure, a securing ring for use with an end-to-end anastomosis stapler includes a first portion including a first tab, a second portion at least partially overlapping the first portion, and an intermediate portion interconnecting the first and second portions. The intermediate portion includes a second tab movable relative to the first tab to reduce a diameter of the securing ring and a ratchet mechanism to selectively maintain the diameter of the securing ring.

In an aspect, the ratchet mechanism may include a hook on the second portion and a plurality of slots defined in the intermediate portion.

In another aspect, the securing ring may be formed as a unitary construct.

In yet another aspect, the securing ring may be formed of a malleable material.

BRIEF DESCRIPTION OF THE DRAWINGS

The above and other aspects and features of this disclosure will become more apparent in view of the following detailed description when taken in conjunction with the accompanying drawings wherein like reference numerals identify similar or identical elements.

DETAILED DESCRIPTION

The surgical stapling device including a securing ring disclosed herein is described in detail with reference to the drawings, in which like reference numerals designate identical or corresponding elements in each of the several views. As used herein, the term "distal" refers to the portion of the device that is being described which is farther from a user in a conventional use of the surgical stapling device, while the term "proximal" refers to the portion of the device that is being described which is closer to a user in a conventional use of the surgical stapling device. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 1:
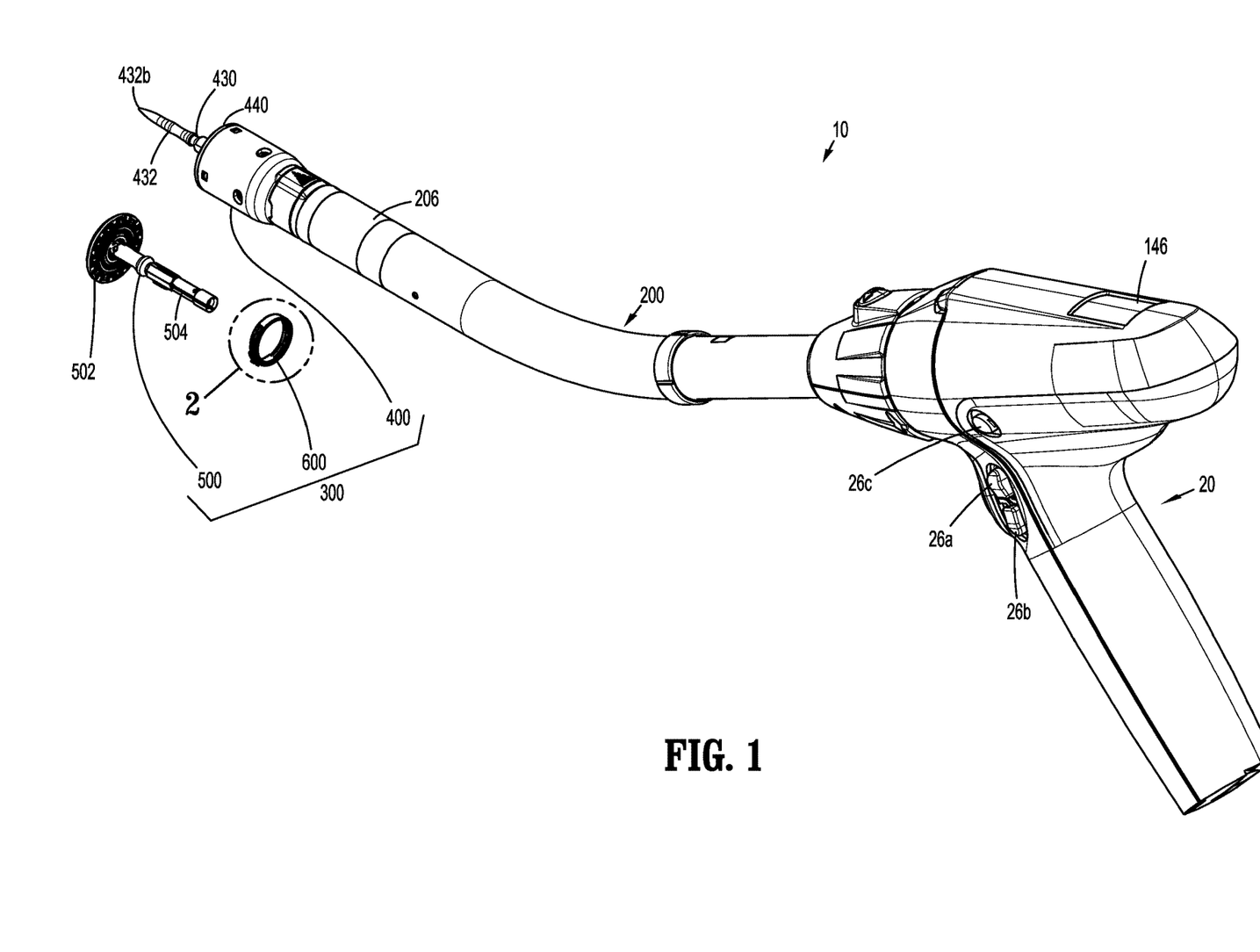
FIG. 1 is a perspective view of a surgical stapling device in accordance with the disclosure, illustrating an anvil assembly and a securing ring separated from a reload of the surgical stapling device.

With reference to FIG. 1, a surgical stapling device 10 for performing circular anastomosis of hollow organs is shown. The surgical stapling device 10 drives a circular array of staples (not shown) through the end sections of each organ and simultaneously fires a cylindrical knife 76 (FIG. 7) to core any tissue radially inward of the driven circular array of staples to free the tubular passage, and thereby joining two ends of the organ (e.g., intestine, colon, etc.). The staples are of a conventional type and include a backspan having a pair of legs extending from the backspan. The legs terminate in tissue penetrating tips. The surgical stapling device 10 includes a handle assembly 20, which is configured for selective connection with an adapter assembly 200. The adapter assembly 200 is configured for selective connection with an end effector 300, which includes a reload 400, an anvil assembly 500, and a securing ring 600 in accordance with the disclosure.

The handle assembly 20 is a powered handle assembly including a main controller circuit board (not shown), a battery (not shown) configured to supply power to any of the electrical components of the handle assembly 20, a plurality of motors (not shown) coupled to the battery, and a display 146. Each of the motors may be coupled to a motor controller which controls the operation of the corresponding motors including the flow of electrical energy from the battery to the motors. A main controller may be provided to control the handle assembly 20. The main controller may be configured to execute software instructions embodying algorithms such as clamping, stapling, and cutting algorithms which control operation of the power handle assembly.

The handle assembly 20 may be actuated to approximate the anvil assembly 500 relative to the reload 400 and to apply a plurality of annular arrays of staples through tissue. The anvil assembly 500 is movable relative to the reload 400 between a spaced apart position and an approximated position, in which, the anvil assembly 500 is positioned adjacent the reload 400 to clamp tissue therebetween. To this end, the handle assembly 20 includes buttons 26a, 26b to cause axial displacement of the anvil assembly 500 between the spaced apart and approximated positions. The handle assembly 20 further includes a button 26c to activate the corresponding motor to fire the staples through tissue to join two segments of tubular tissue together, as will be described below.

The adapter assembly 200 is configured to convert rotational output of the motors of the handle assembly 20 into axial translations useful for operating the end effector 300. The adapter assembly 200 includes a trocar assembly 430 supported in a distal end of an outer tube 206. The trocar assembly 430 includes a trocar member 432 movable axially relative to the outer tube 206. A distal end 432b of the trocar member 432 is configured to selectively engage the anvil assembly 500, such that axial movement of the trocar member 432 results in a concomitant axial displacement of the anvil assembly 500.

The reload 400 includes a staple cartridge assembly 410 that defines a plurality of annular arrays of staple receiving slots having a staple (not shown) disposed in each one of the staple receiving slots. In addition, the staple cartridge assembly 410 includes a cylindrical knife 76 (FIG. 7) that is concentrically arranged with the annular arrays of staples (not shown) and a plurality of staple pushers (not shown) each disposed in the respective staple receiving slot to eject the respective staple through the staple receiving slot. The cylindrical knife 76 is adapted to cut tissue. In use, the staples travel through the staple receiving slots and tissue towards the anvil assembly 500 for formation thereof. Upon actuation of the surgical stapling device 10, the cylindrical knife 76 is moved distally to cut tissue, and the plurality of pushers (not shown) are displaced distally to eject the staples disposed in the staple receiving slots therethrough, towards the anvil assembly 500.

Positioned distally of the staple cartridge assembly 410 is the anvil assembly 500 including an anvil member 502 and an anvil shaft 504 extending proximally from the anvil member 502. The anvil member 502 further defines a plurality of pockets 505 (FIG. 6) for receiving and forming the staples. The anvil shaft 504 is configured to detachably receive the trocar member 432 of the trocar assembly 430 of the staple cartridge assembly 410. The trocar assembly 430 is operatively coupled with the handle assembly 20, whereby activation of the corresponding motor (not shown) in the handle assembly 20 causes axial displacement of the trocar member 432 of the trocar assembly 430. Such axial displacement of the trocar member 432 is imparted to the anvil assembly 500 detachably coupled with the trocar assembly 430. In this manner, the anvil assembly 500 is axially movable relative to the staple cartridge assembly 410 between the spaced apart position and the approximated position, in which, the anvil assembly 500 is positioned adjacent the staple cartridge assembly 410 to clamp tissue between the anvil assembly 500 and the staple cartridge assembly 410. Examples of devices for performing circular anastomosis of hollow organs are described in U.S. Pat. Nos. 6,053,390, 5,588,579, 5,119,983, and 5,005,749 and U.S. Patent Publication No. 2018/0360460, each of which is incorporated herein in its entirety by reference.

Figure 2:
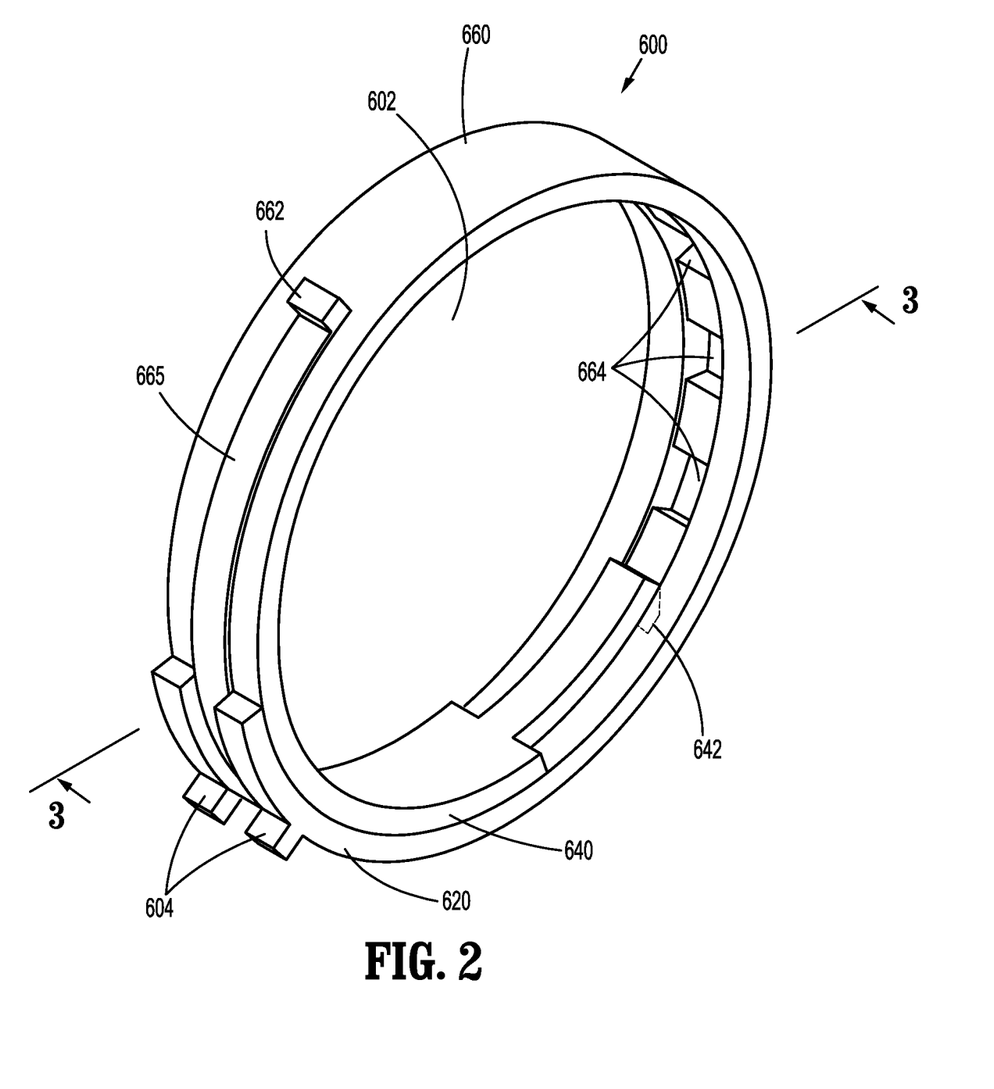
FIG. 2 is an enlarged view of the indicated area of detail of FIG. 1.
Figure 3:
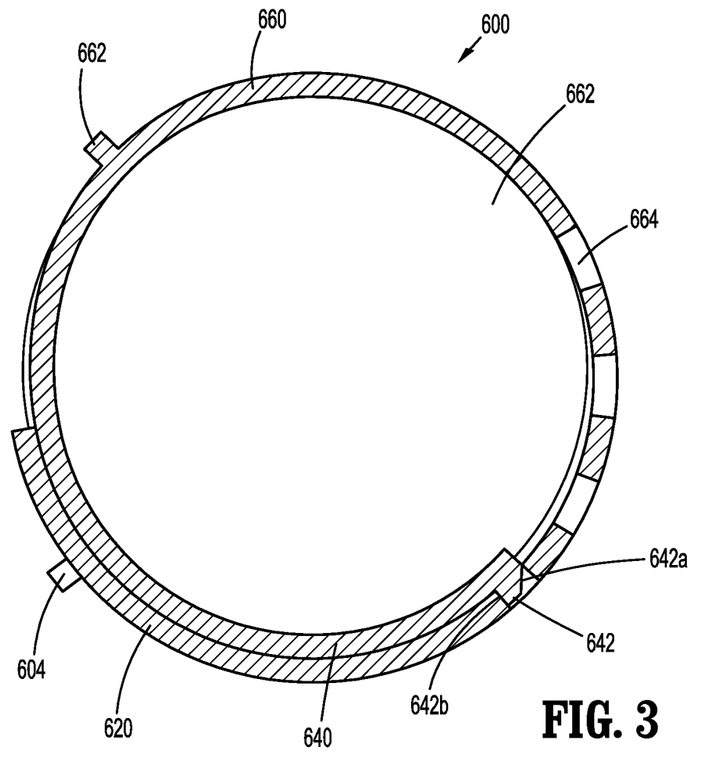
FIG. 3 is a cross-sectional view of the securing ring of FIG. 2 taken along section line 3-3 of FIG. 2.

FIGS. 2 and 3 illustrate the securing ring 600 of the end effector 300 of the surgical stapling device 10 in accordance with the disclosure. The securing ring 600 is utilized to secure the anvil shaft 504 of the anvil assembly 500 (FIG. 1) to tissue. The securing ring 600 has an annular profile defining an aperture 602. A diameter of the aperture 602 may be selectively adjustable by the clinician to secure the anvil assembly 500 to a tubular tissue, as will be described below. In particular, the securing ring 600 has a first portion 620, a second portion 640, and an intermediate portion 660 that interconnects the first and second portions 620, 640. In an aspect, the securing ring 600 is formed as a single construct. In another aspect, the securing ring 600 is monolithically formed as a unitary construct. In another aspect, the securing ring 600 is formed from thermoplastics including polycarbonates, and metals including stainless steel and aluminum. In another aspect, the securing ring 600 may be flexible or malleable.

The first and second portions 620, 640 at least partially overlap each other. The first and second portions 620, 640 may be movable relative to each other to selectively adjust a diameter of the aperture 602. The first portion 620 has first tabs 604 and the intermediate portion 660 has a second tab 662. The intermediate portion 660 defines an elongate slot 665 (FIG. 2) to facilitate flexing or overlapping of the first and second portions 620, 640. The second portion 640 has a hook 642 that defines a tapered surface 642a and a locking surface 642b. The intermediate portion 660 defines slots 664 that are circumferentially arranged. Each slot 664 is configured to receive the hook 642, thereby defining a ratchet mechanism. Under such a configuration, when the first and second tabs 604 are moved towards each other, the tapered portion 642a of the hook 642 slides over the slots 664. When the desired diameter of the aperture 602 is achieved, the first and second tabs 604, 662 are released such that the locking surface 642b of the hook 642 is secured within the corresponding slot 664. In this manner, the desired diameter of the aperture 602 is achieved and maintained.

Figure 4:
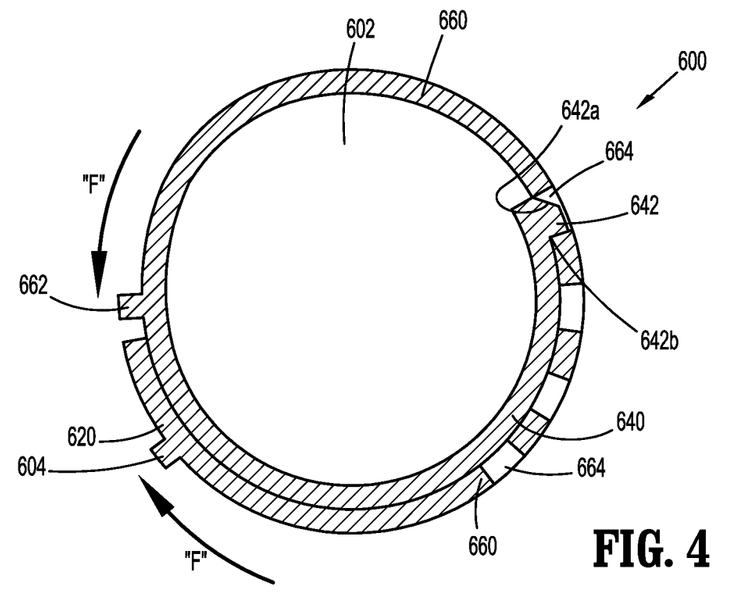
FIG. 4 is a cross-sectional view of the securing ring of FIG. 3, illustrating reduction of a diameter of the securing ring.

For example, as shown in FIG. 4, when the first tabs 604 (only one shown) of the first portion 620 and the second tab 662 of the intermediate portion 660 are moved towards each other in the direction of arrows "F", the hook 642 slides over the slots 664, which reduces the diameter of the aperture 602 until the desired diameter is achieved. In this manner, the diameter of the aperture 602 may be selectively adjustable by a clinician. For example, surgical graspers (not shown) may be utilized to move the first and second tabs 604, 662 towards each other to achieve the desired diameter of the aperture 602.

Figures 5, 6:
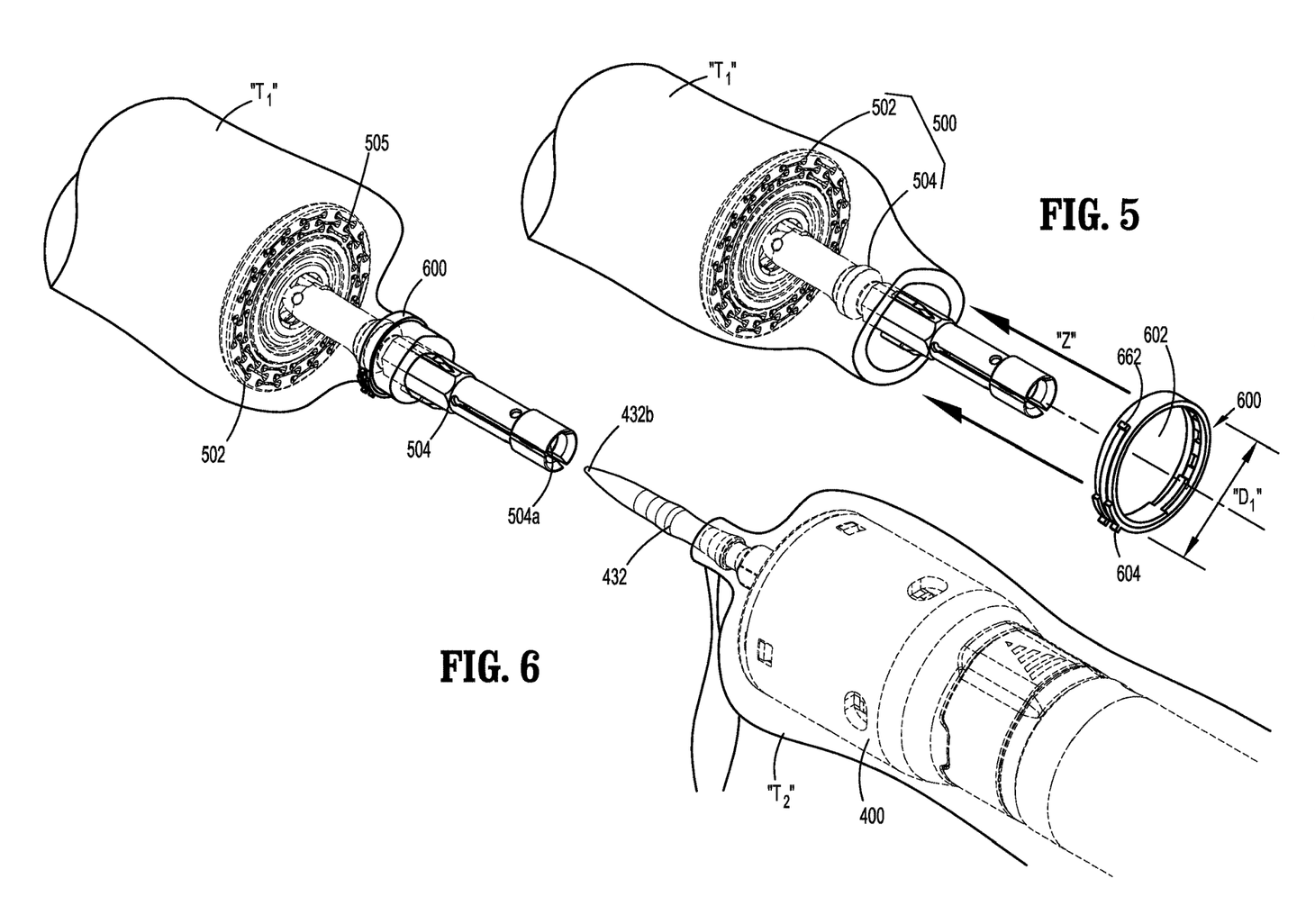
FIG. 5 is a perspective view of the anvil assembly and the securing ring of FIG. 1, illustrating use thereof with tissue.
FIG. 6 is a perspective view of the anvil assembly, the securing ring, and the reload of FIG. 1, illustrating use thereof with tissue.

In use, the anvil assembly 500 is at least partially placed in a first tubular section "$T_1$" of tissue such that the anvil shaft 504 extends through an opening of the first tubular section "$T_1$", as shown in FIG. 5. The securing ring 600 is then placed over the anvil shaft 504 and the first tubular section "$T_1$" disposed about the anvil shaft 504. Specifically, the anvil shaft 504 and a portion of the first tubular section "$T_1$" extend through the aperture 602 (FIG. 5) of the securing ring 600 having a first diameter "$D_1$". At this time, the clinician may reduce a diameter of the aperture 602 of the securing ring 600 to secure the anvil assembly 500 to the first tubular section "$T_1$" by sliding the first and second tabs 604, 662 of the securing ring 600 towards each other until the securing ring 600 secures the anvil assembly 500 to the first tubular section "$T_1$" as shown in FIG. 6.

As shown in FIG. 6, the reload 400 is placed in a second tubular section "$T_2$" of tissue such that the trocar member 432 extends through an opening of the second tubular section "$T_2$". An end of the second tubular section "$T_2$" may be secured to the trocar member 432 by a suture "S". Alternatively, the securing ring 600 may be utilized to secure the second tubular section "$T_2$" to the trocar member 432. The distal end 432b of the trocar member 432 of the reload 400 is placed into a channel 504a of the annular shaft 504 such that the anvil shaft 504 is attached to the trocar member 432. The anvil shaft 504 engages the trocar assembly 430 to be operable as a unitary construct. The anvil assembly 500 and the reload 400 are then approximated to approximate the first and second tubular sections "$T_1$", "$T_2$".

Figure 7:
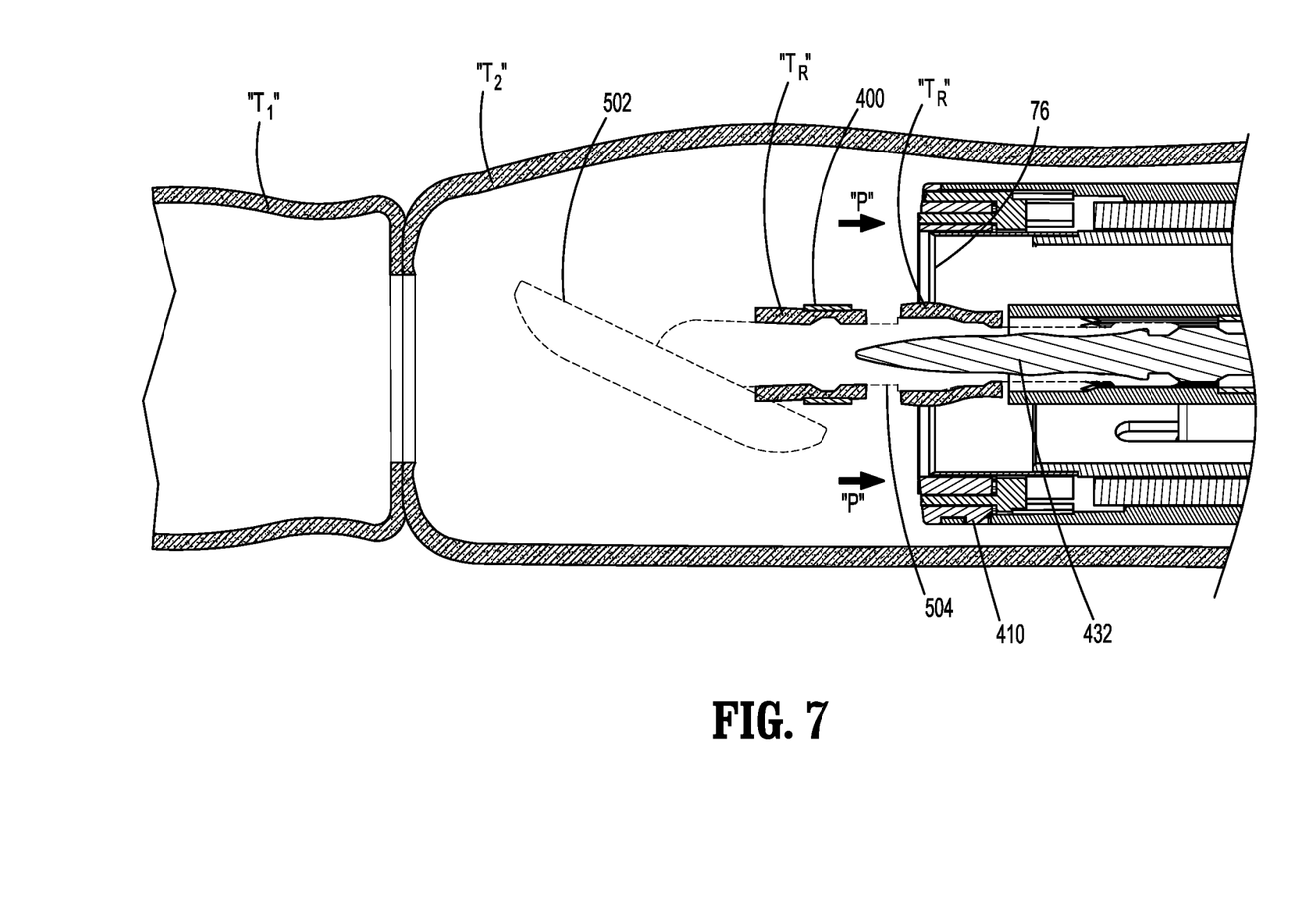
FIG. 7 is a side cross-sectional view of the reload of FIG. 6, illustrating removal of the surgical stapling device from stapled tubular sections of tissue.

Under such a configuration, the clinician may begin the clamping process on tissue interposed between the reload 400 and the anvil assembly 500 by pressing the button 26a (FIG. 1) on the handle assembly 20. Once clamping is successfully completed, the clinician initiates the stapling sequence. To initiate stapling sequence, the clinician presses the button 26c (FIG. 1). The surgical stapling device 10 is then fired causing the plurality of staple pushers each disposed in respective staple receiving slot to eject the respective staple through the slot. Staples are ejected from the staple cartridge assembly 410 and pierce through tissue to be formed against the anvil member 502. Specifically, the staples travel through the first and second tubular sections "$T_1$", "$T_2$" towards the anvil assembly 500, thereby effecting stapling of the first and second tubular section "$T_1$", "$T_2$" to one another, while the cylindrical knife 76 cuts a portion of tissue disposed radially inward of the cylindrical knife 76 to complete the anastomosis. Upon completion, the anvil member 502 may be tilted and the reload and the anvil assembly 500 may be retracted in the direction of arrows "P" to be removed from the first and second tubular sections T1, T2 of tissue, as shown in FIG. 7. The securing ring 600 along with resected tissue "$T_R$" remain on the anvil shaft 504.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. For example, the securing ring 600 may be utilized in a robotic surgery. Those skilled in the art will envision other modifications within the scope and spirit of the claims appended hereto.

What is claimed is:

1. A surgical kit comprising:
a stapling device including:
a reload including a trocar member configured for axial displacement; and
an anvil assembly including an anvil and an anvil shaft detachably couplable to the trocar member of the reload for unitary movement, the anvil being transitionable between a spaced apart position and an approximated position configured to clamp tissue between the anvil and the reload; and
a securing ring selectively securable about the anvil shaft, the securing ring having an annular profile defining an aperture, the securing ring including first and second portions and an intermediate portion interconnecting the first and second portions, the first and second portions adjustably overlapping each other, the first portion including a first tab, the second portion including a hook, the intermediate portion including a second tab and defining a plurality of slots to receive the hook of the second portion, wherein when the first and second tabs are displaced relative to each other, the aperture of the securing ring is transitionable from a first state having a first diameter to a second state having a second diameter.

2. The surgical kit according to claim 1, wherein when the first and second tabs are displaced towards each other, the first diameter is larger than the second diameter.

3. The surgical kit according to claim 1, wherein the securing ring is formed as a single construct.

4. The surgical kit according to claim 1, wherein the securing ring is monolithically formed as a unitary construct.

5. The surgical kit according to claim 1, wherein the plurality of slots of the intermediate portion are circumferentially arranged about the securing ring.

6. The surgical kit according to claim 1, wherein the hook of the securing ring includes a tapered portion configured to slide over the plurality of slots of the intermediate portion of the securing ring when the first and second tabs are displaced towards each other.

7. The surgical kit according to claim 6, wherein the hook includes a locking surface to be received in one slot of the plurality of slots of the intermediate portion of the securing ring to maintain a diameter of the aperture of the securing ring.

8. The surgical kit according to claim 1, wherein the anvil shaft of the anvil assembly defines a channel to receive the trocar member of the reload.

9. The surgical kit according to claim 1, wherein the intermediate portion defines an elongate slot to facilitate flexing of the securing ring.

10. A surgical kit comprising:
a surgical stapling device including an adapter having:
an elongate shaft;
a reload supported on a distal end portion of the elongate shaft, the reload including a trocar member axially movable; and
an anvil assembly including an anvil and an anvil shaft, the anvil shaft being releasably attachable to the trocar member; and
a securing ring selectively securable about the anvil shaft, the securing ring having an annular profile defining an aperture, the securing ring including first and second portions that at least partially overlap each other, the securing ring having tabs that are movable relative to each other, thereby selectively transitioning the aperture between a first diameter and a second diameter.

11. The surgical kit according to claim 10, wherein the securing ring further includes a ratchet mechanism to selectively maintain a diameter of the aperture.

12. The surgical kit according to claim 10, wherein the securing ring defines a circumferential slot to facilitate flexing of the securing ring.

13. The surgical kit according to claim 10, wherein when the tabs are displaced towards each other, a diameter of the aperture of the securing ring is reduced.

14. The surgical kit according to claim 10, wherein the securing ring is monolithically formed.

15. The surgical kit according to claim 10, wherein the anvil shaft is movable with the trocar member as a unitary construct when the anvil shaft is coupled to the trocar member.

16. The surgical kit according to claim 10, wherein the securing ring is formed of a malleable material.

17. A securing ring for use with an end-to-end anastomosis stapler the securing ring comprising:
a first portion including a first tab;
a second portion at least partially overlapping the first portion; and
an intermediate portion interconnecting the first and second portions, the intermediate portion including a second tab movable relative to the first tab to reduce a diameter of the securing ring and a ratchet mechanism to selectively maintain the diameter of the securing ring.

18. The securing ring according to claim 17, wherein the ratchet mechanism includes a hook on the second portion and a plurality of slots defined in the intermediate portion.

19. The securing ring according to claim 17, wherein the securing ring is formed as a unitary construct.

20. The securing ring according to claim 17, wherein the securing ring is formed of a malleable material.

* * * * *